US009682228B2

(12) United States Patent
 Dubuclet (10) Patent No.: US 9,682,228 B2
(45) Date of Patent: *Jun. 20, 2017

(54) IMPLANTABLE LEAD WITH FLEXIBLE PADDLE ELECTRODE ARRAY

(71) Applicant: ADVANCED NEUROMODULATION SYSTEMS, INC., Plano, TX (US)

(72) Inventor: Jodi Townsley Dubuclet, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/151,397

(22) Filed: May 10, 2016

(65) Prior Publication Data

US 2016/0250461 A1    Sep. 1, 2016

Related U.S. Application Data

(62) Division of application No. 14/479,066, filed on Sep. 5, 2014, now Pat. No. 9,358,384.

(51) Int. Cl.
 *A61N 1/05* (2006.01)
(52) U.S. Cl.
 CPC .................................. *A61N 1/0553* (2013.01)
(58) Field of Classification Search
 CPC ..................................................... A61N 1/0553
 USPC ................................................. 607/115–117
 See application file for complete search history.

(56) References Cited

U.S. PATENT DOCUMENTS

| 7,006,875 | B1* | 2/2006 | Kuzma | A61N 1/0556 |
| | | | | 600/372 |
| 8,099,172 | B2* | 1/2012 | Swanson | A61N 1/0553 |
| | | | | 607/116 |
| 8,244,374 | B1* | 8/2012 | Swanson | A61N 1/0553 |
| | | | | 607/117 |
| 9,084,882 | B1* | 7/2015 | Raines | A61N 1/0553 |
| 2007/0055336 | A1* | 3/2007 | Greenberg | A61N 1/0543 |
| | | | | 607/141 |
| 2007/0060991 | A1* | 3/2007 | North | A61N 1/0553 |
| | | | | 607/117 |
| 2008/0046051 | A1* | 2/2008 | Skubitz | A61N 1/0553 |
| | | | | 607/115 |
| 2009/0099439 | A1* | 4/2009 | Barolat | A61B 5/04001 |
| | | | | 600/372 |
| 2009/0293270 | A1* | 12/2009 | Brindley | A61N 1/05 |
| | | | | 29/829 |
| 2010/0094387 | A1* | 4/2010 | Pianca | A61N 1/0553 |
| | | | | 607/116 |
| 2012/0053645 | A1* | 3/2012 | Ayanoor-Vitikkate | A61N 1/36064 |
| | | | | 607/2 |
| 2012/0071936 | A1* | 3/2012 | Pianca | A61N 1/0553 |
| | | | | 607/2 |

(Continued)

Primary Examiner — Allen Porter, Jr.

(57) ABSTRACT

A neurostimulation system is disclosed herein. The neurostimulation system includes an implantable pulse generator and an implantable therapy lead configured to be electrically coupled to the implantable pulse generator. The implantable therapy lead includes a flexible paddle electrode array with flexible electrodes. Each flexible electrode has a segmented configuration having first and second electrode segments and a flexible bridge or living hinge joining together the first and second electrode segments.

5 Claims, 9 Drawing Sheets

(56) References Cited

U.S. PATENT DOCUMENTS

| | | | | |
|---|---|---|---|---|
| 2012/0316610 A1* | 12/2012 | Pianca | ............... | A61N 1/0553 |
| | | | | 607/2 |
| 2012/0330393 A1* | 12/2012 | Janik | ............... | A61N 1/0551 |
| | | | | 607/148 |
| 2014/0172057 A1* | 6/2014 | Orinski | ............... | A61N 1/0553 |
| | | | | 607/116 |
| 2014/0277311 A1* | 9/2014 | Victorine | ............... | A61N 1/05 |
| | | | | 607/116 |
| 2014/0379043 A1* | 12/2014 | Howard | ............... | A61N 1/0553 |
| | | | | 607/46 |
| 2015/0066122 A1* | 3/2015 | Govea | ............... | A61N 1/05 |
| | | | | 607/116 |

* cited by examiner

IMPLANTABLE LEAD WITH FLEXIBLE PADDLE ELECTRODE ARRAY

CROSS REFERENCE TO RELATED APPLICATIONS

This is a division of U.S. patent application Ser. No. 14/479,066, filed Sep. 5, 2014.

FIELD OF THE INVENTION

The present disclosure relates to medical apparatus and methods. More specifically, the present disclosure relates to neurostimulation methods and systems, and more particularly to paddle leads

BACKGROUND OF THE INVENTION

Application of electrical fields to spinal nerve roots, spinal cord, and other nerve bundles for the purpose of chronic pain control has been actively practiced for some time. While a precise understanding of the interaction between applied electrical energy and the neural tissue is not understood, application of an electrical field to spinal nervous tissue (i.e., spinal nerve roots and spinal cord bundles) can effectively mask certain types of pain transmitted from regions of the body associated with the stimulated nerve tissue. Specifically, applying electrical energy to regions of the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Each exterior region, or each dermatome, of the human body is associated with a particular spinal nerve root at a particular longitudinal spinal position. The head and neck regions are associated with C2-C8, the back regions extend from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position. For example, to address chronic pain sensations that commonly focus on the lower back and lower extremities using conventional techniques, a specific energy field is typically applied to a region between vertebrae levels T8 and T12. The specific energy field often stimulates a number of nerve fibers and structures of the spinal cord. By applying energy in this manner, the patient commonly experiences paresthesia over a relatively wide region of the patient's body from the lower back to the lower extremities.

Positioning of an applied electrical field relative to a physiological midline is also important. Nerve fibers extend between the brain and a nerve root along the same side of the dorsal column that the peripheral areas the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral". Accordingly, bilateral pain is addressed through application of electrical energy along both sides of the column and/or along a patient's physiological midline.

Implantable leads have conductors extending therethrough that place distal electrodes of the lead in electrical communication with implantable pulse generators (IPGs) from which the implantable leads distally extend. The distal electrodes of the leads are positioned adjacent to pertinent nerves such that the electrodes deliver stimulation pulses to the nerves, those stimulation pulses originating from the IPGs and transmitted to the distal electrodes via the conductors of the leads.

To supply suitable pain-managing electrical energy, multi-programmable IPGs enable a pattern of electrical pulses to be varied across the electrodes of a lead. Specifically, such systems enable electrodes of a connected stimulation lead to be set as an anode (+), as a cathode (−), or to a high-impedance state (OFF). As is well known, negatively charged ions and free electrons flow away from a cathode toward an anode. Consequently, a range of very simple to very complex electrical fields can be created by defining different electrodes in various combinations of (+), (−), and OFF. Of course, in any instance, a functional combination must include at least one anode and at least one cathode (although in some cases, the "can" of the IPG can function as an anode).

Percutaneous leads and paddle leads are the two most common types of lead designs that provide conductors to deliver stimulation pulses from an implantable pulse generator (IPG) to distal electrodes adjacent to the pertinent nerve tissue. Example commercially available leads include the QUATTRODE™, OCTRODE™, LAMITRODE™, TRIPOLE™, EXCLAIM™, and PENTA™ stimulation leads from St. Jude Medical, Inc.

A conventional percutaneous lead includes electrodes that substantially conform to the body of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

A conventional laminotomy or paddle lead has a paddle configuration and typically possesses a plurality of electrodes (commonly, eight, or sixteen) arranged in columns. Due to their dimensions and physical characteristics, conventional paddle leads may require a surgical procedure (a partial laminectomy) for implantation. Multi-column paddle leads enable more reliable positioning of a plurality of electrodes as compared to percutaneous leads. Also, paddle leads offer a more stable platform that tends to migrate less after implantation. Paddle leads are capable of being sutured in place. Paddle leads also create a uni-directional electrical field and, hence, can be used in a more electrically efficient manner than at least some known percutaneous leads.

Conventional laminotomy or paddle leads may be configured to employ paddle electrode arrays having a plurality of electrodes, which may be in the form of rectangular planar electrodes. Although a staggered electrode arrangement can provide superior electrode coverage as compared to that of a non-staggered electrode arrangement, a paddle electrode array with a staggered electrode arrangement will have reduced flexibility as compared to a similar paddle electrode array with a non-staggered electrode arrangement. The more rigid the paddle electrode array, the more likely the paddle electrode array can result in trauma to the epidural space in which it is implanted.

Accordingly, there is a need in the art for a paddle electrode array offering improved electrode coverage while still offering appropriate flexibility.

SUMMARY

A neurostimulation system is disclosed herein. In one embodiment, the neurostimulation system includes an implantable pulse generator and an implantable therapy lead configured to be electrically coupled to the implantable pulse generator. The implantable therapy lead includes a flexible paddle electrode array with flexible electrodes. Each flexible electrode has a segmented configuration having first and second electrode segments and a flexible bridge or living hinge joining together the first and second electrode segments.

In one embodiment, the flexible paddle electrode array also includes nonflexible electrodes that do not extend across flex lines of the flexible paddle electrode array. The flex lines extend generally perpendicular to the longitudinal length of the flexible paddle electrode array to pass through the flexible bridges. The flex lines are locations along the length of the flexible paddle electrode array where the array can flex. Because the nonflexible electrodes do not extend across the flex lines, and the flexible bridges of the flexible electrodes are aligned with the flex lines such that the bridges can act as living hinges to allow the electrode segments of the flexible electrodes to flex relative to each other at their respective living hinges, the flexible paddle electrode array can flex or bend along the various flex lines.

Another neurostimulation system is disclosed herein. In one embodiment, the neurostimulation system includes an implantable pulse generator and an implantable therapy lead configured to be electrically coupled to the implantable pulse generator. The implantable therapy lead includes a flexible paddle electrode array that has a row of laterally aligned flexible electrodes and a row of laterally aligned nonflexible electrodes. The row of laterally aligned flexible electrodes at least partially contributes to the formation of a flex line in the flexible paddle electrode. The row of laterally aligned nonflexible electrodes is longitudinally offset from the row of laterally aligned flexible electrodes such the flex line does not extend across the row of laterally aligned nonflexible electrodes.

In one embodiment, a flexible electrode of the flexible electrodes may include a first electrode segment and a second electrode segment spaced-apart from the first electrode segment. The flex line passes between the spaced-apart first and second electrode segments.

The flexible electrode of the flexible electrodes may further include a flexible living hinge joining the spaced-apart first and second electrode segments. The flex line passes through the flexible living hinge. The flexible living hinge may include a V-shape or U-shape.

The flexible electrode may be of an integrated construction such that at least one of the first electrode segment, the second electrode segment or the flexible living hinge are separate pieces joined together during manufacturing of the flexible electrode. The joining together during manufacturing of the flexible electrode may include at least one of welding or crimping.

Alternatively, the flexible electrode may be of a unitary and continuous construction such that the first electrode segment, the second electrode segment and the flexible living hinge are formed from a single material piece during manufacturing of the flexible electrode. The forming during manufacturing of the flexible electrode may include at least one of stamping or laser cutting.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Neurostimulation systems 5 and methods are disclosed herein. In addition to an implantable pulse generator (IPG) 310, the neurostimulation system 5 also includes an implantable therapy lead 10 that is capable of being coupled to the IPG 310. As discussed in detail below, in one embodiment, the lead 10 includes a flexible paddle electrode array 11 that includes nonflexible electrodes 36 and flexible electrodes 38. Each flexible electrode 38 includes first and second electrode segments 68A, 68B and a living hinge 70 that joins together the electrode segments 68A, 68B to allow the electrode segments 68A, 68B to flex or articulate relative to each other about the living hinge 70, but still remain in solid contact with patient tissue.

The nonflexible electrodes 36 are grouped into rows of laterally aligned nonflexible electrodes 36 on the flexible paddle electrode array 11. Similarly, the flexible electrodes 38 are grouped into rows of laterally aligned flexible electrodes 38 on the flexible paddle electrode array 11. The even longitudinal spacing of the rows of laterally aligned nonflexible electrodes 36 is offset or staggered from the even longitudinal spacing of the rows of laterally aligned flexible electrodes 38. Further, the living hinges 70 of each row of laterally aligned flexible electrodes 38 are aligned along a flex or hinge line 100 of the flexible paddle array 11. Since no portion of a nonflexible electrode 36 extends across these flex or hinge lines 100, the flexible paddle electrode array 11 has transverse lines of reduced rigidity or stiffness at these flex or hinge lines 100, thereby allowing the flexible paddle electrode array 11 to flex or deflect along its length at these hinge lines 100. Because of the living hinges 70, the staggered arrangement of the rows of the nonflexible and flexible electrodes, and the flex or hinge lines 100, the flexible paddle electrode array 11 is able to flex along its length, but be sufficiently rigid to maintain the nonflexible and flexible electrodes in adequate contact with patient tissue.

A. DEFINITIONS

Unless defined otherwise, technical and scientific terms used herein have the same meaning as commonly understood by one of ordinary skill in the art to which this disclosure belongs. For purposes of the present disclosure, the following terms are defined below.

As used herein, the use of the word "a" or "an" when used in conjunction with the term "comprising" in the claims and/or the specification may mean "one", but it is also consistent with the meaning of "one or more," "at least one", and "one or more than one". Still further, the terms "having", "including", "containing" and "comprising" are interchangeable and one of skill in the art is cognizant that these terms are open-ended terms. Some embodiments may consist of or consist essentially of one or more elements, method steps, and/or methods of the disclosure. It is contemplated that any method or composition described herein can be implemented with respect to any other method or composition described herein.

As used herein, the use of the term "dorsal column" refers to conducting pathways in the spinal cord that are located in the dorsal portion of the spinal cord between the posterior horns, and which includes afferent somatosensory neurons. The dorsal column is also known as the posterior funiculus.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T1 nerve root leaves the spinal cord myelum at an area located behind vertebral body T8-T9 but leaves the bony spine between T11 and T12.

As used herein the term "chronic pain" refers to a persistent state of pain experienced for a substantial amount of time (e.g., longer than three months).

As used herein the term "complex regional pain syndrome" or "CRPS" refers to painful conditions that usually affect the distal part of an upper or lower extremity and are associated with characteristic clinical phenomena. CRPS is divided into two subtypes CRPS Type I and CRPS Type II. Generally, the clinical characteristics of Type I are the same as seen in Type II. The central difference between Type I and Type II is that Type II typically occurs following a sensory nerve injury whereas Type I occurs in the absence of any known nerve injury.

B. ORGANIZATION OF NERVOUS SYSTEM

The nervous system includes two general components, the central nervous system, which is composed of the brain and the spinal cord, and the peripheral nervous system, which is composed of ganglia or dorsal root ganglia and the peripheral nerves that lie outside the brain and the spinal cord. Those of skill in the art will appreciate that the components of the nervous system may be linguistically separated and categorized, but functionally they are interconnected and interactive.

Figure 1A:
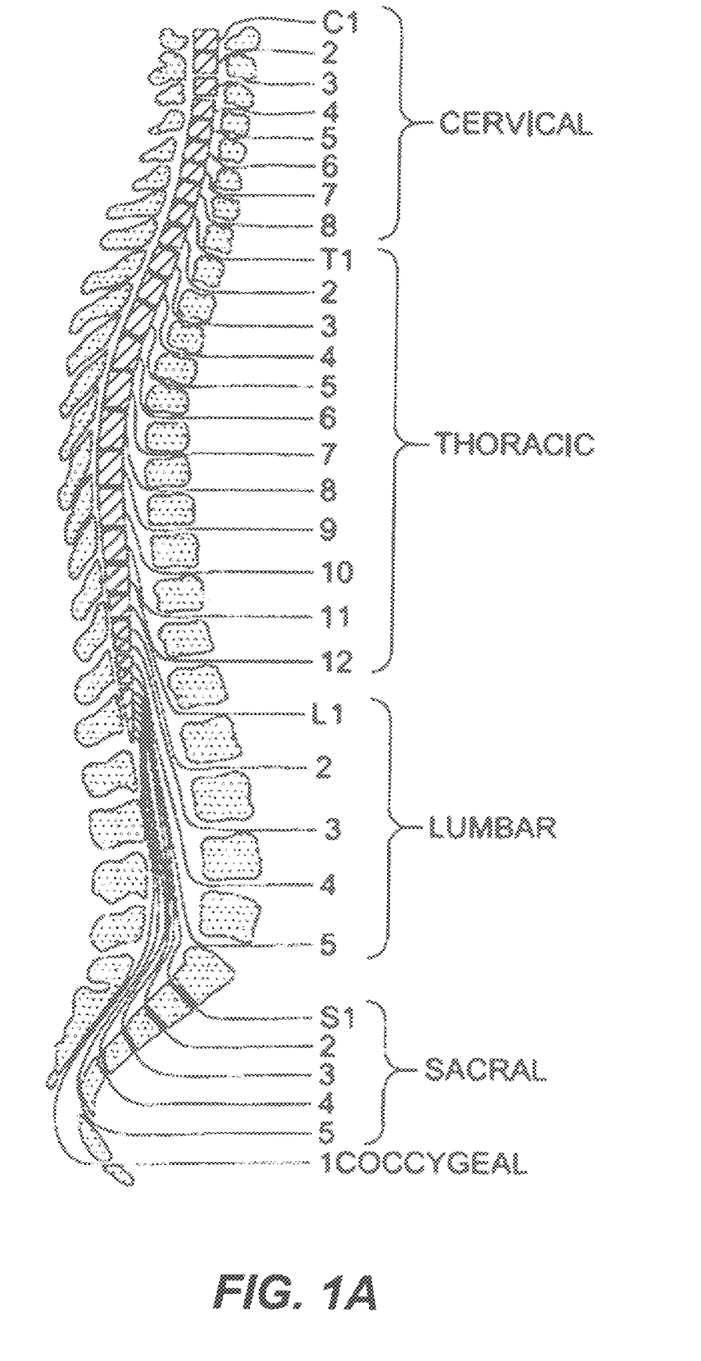
FIG. 1A is a schematic diagram of the spinal cord and the nerve roots in relation to the vertebral spinal canal.

The central nervous system includes the brain and spinal cord, which together function as the principal integrator of sensory input and motor output. In general terms, the brain consists of the cerebrum (cerebral hemispheres and the diencephalons), the brainstem (midbrain, pons, and medulla), and the cerebellum. The spinal cord is organized into segments, for example, there are eight cervical (C1-C8), 12 thoracic (T1-T12), five lumbar (L1-L5), five sacral (S1-S5), and one cocygeal (Co1) spinal segments. In adults, the spinal cord typically ends at the level of the L1 or L2 vertebral bones. As shown in FIG. 1A, which is a is a schematic diagram of the spinal cord and the nerve roots in relation to the vertebral spinal canal, the nerve roots travel downward to reach their exit points at the appropriate levels. Left and right sensory and motor nerve roots arise from each segment of the spinal cord except for the C1 and Co1 segments, which have no sensory roots. Associated sensory and motor nerve roots fuse to form a single mixed spinal nerve for each segment. The mixed spinal nerves further fuse and intermingle peripherally to form plexuses and nerve branches.

The peripheral nervous system is divided into the autonomic system (parasympathetic and sympathetic), the somatic system, and the enteric system. The term peripheral nerve is intended to include both motor and sensory neurons and neuronal bundles of the autonomic system, the somatic system, and the enteric system that reside outside of the spinal cord and the brain. Peripheral nerve ganglia and nerves located outside of the brain and spinal cord are also described by the term peripheral nerve.

C. OVERVIEW OF NEUROSTIMULATION SYSTEM

Figure 1B:
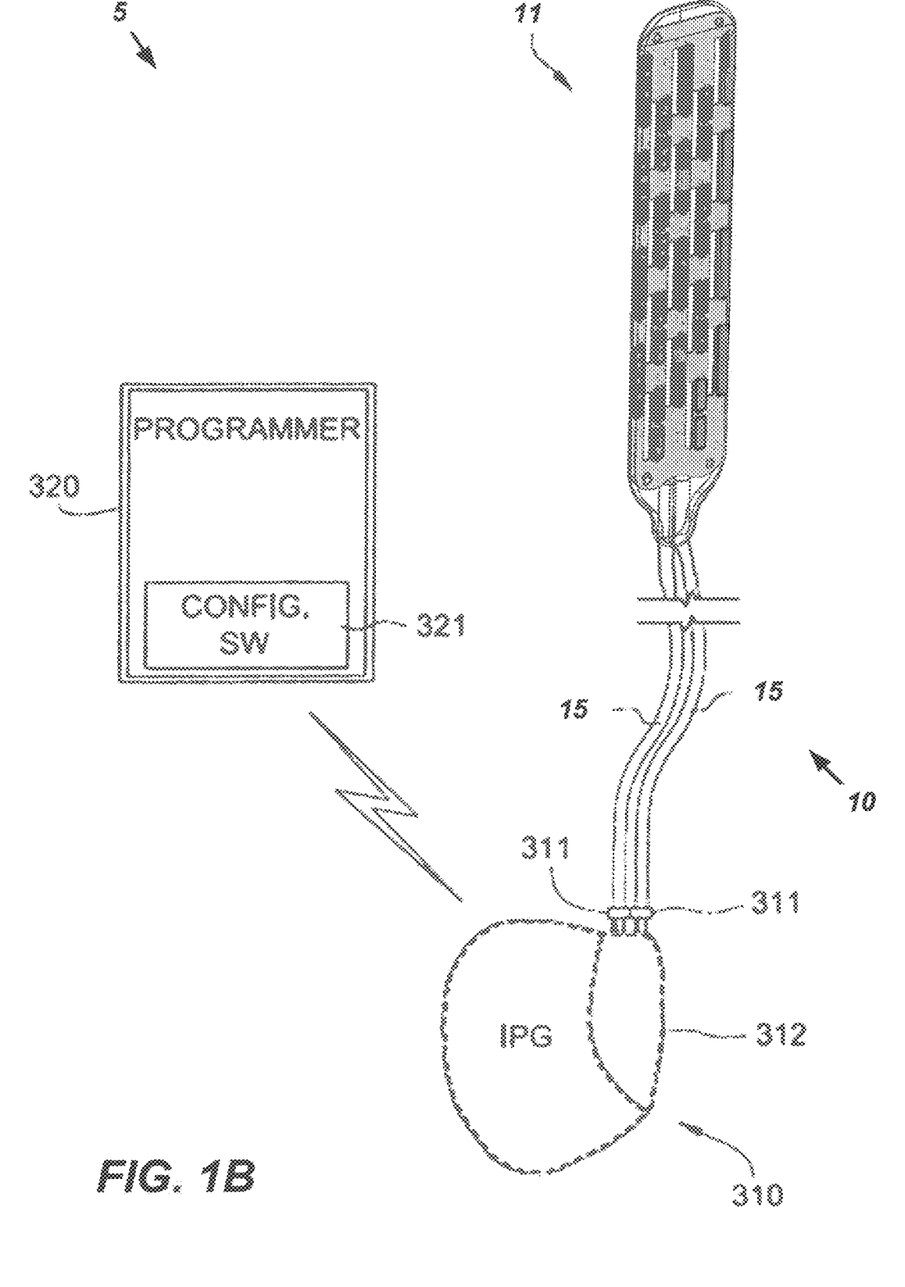
FIG. 1B is a schematic diagram of a neurostimulation system including a paddle lead extending from an implantable pulse generator in communication with a wireless programmer.

FIG. 1B is a schematic diagram of a neurostimulation system 5 including a paddle lead 10, an implantable pulse generator (IPG) 310, and a programmer 320. The paddle lead 10 extends from the IPG 310. The programmer 320 is in wireless communication with the IPG 310. An example of a commercially available IPG 310 is the Eon™ Rechargeable IPG from St. Jude Medical, Inc. (Plano, Tex.), although any suitable IPG, such as RF powered devices, could be alternatively employed.

Figure 1C:
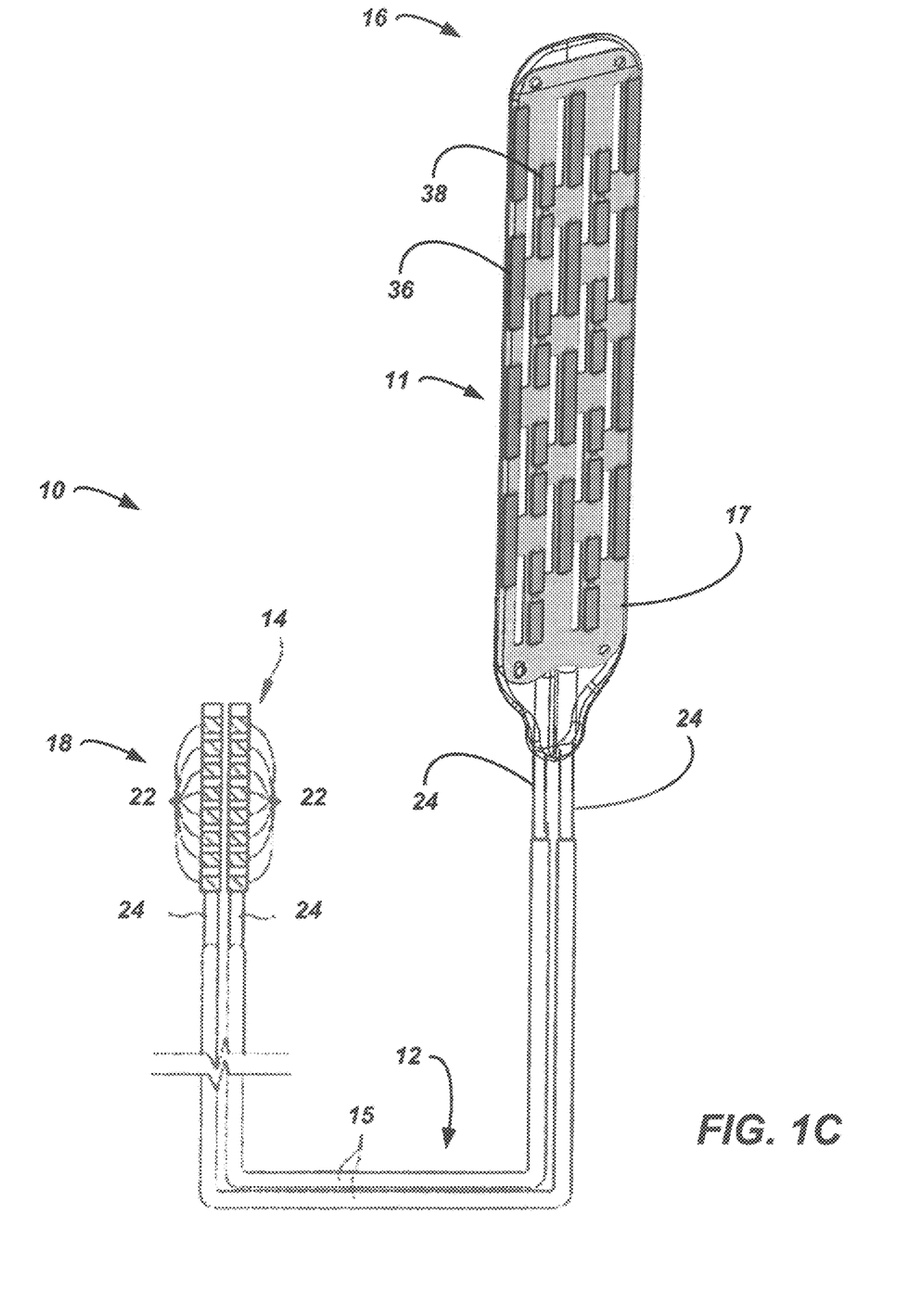
FIG. 1C is a schematic diagram of the paddle lead of FIG. 1B, wherein the paddle lead has a flexible paddle electrode array.

FIG. 1C is a schematic diagram of the paddle lead 10 employed in the system 5 of FIG. 1B, according to one embodiment. The paddle lead 10 includes a proximal end 14 and a distal end 16. The proximal end 14 includes a connector end or assembly 18 with a plurality of electrically conductive terminals 22. The distal end 16 includes a flexible paddle electrode array 11 that includes a plurality of nonflexible electrodes 36 and flexible electrodes 38 arranged within a substantially flat and thin paddle style structure 17. The electrodes 36, 38 are mutually separated by the electrically insulative material of the paddle 17. Further details regarding the flexible paddle electrode array 11 and its construction are given below.

A lead body 12 of the lead 10 extends between the flexible paddle electrode array 11 and the connector end 18. Conductors 24, which are embedded within respective insulative sheaths 15 of the insulative lead body 12, electrically connect the electrodes 36, 38 to the terminals 22.

The terminals 22 are preferably formed of a non-corrosive, highly conductive material. Examples of such material include stainless steel, MP35N, platinum, and platinum alloys. In one embodiment, the terminals 22 are formed of a platinum-iridium alloy.

Each conductor 24 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, one embodiment uses conductors 24 formed of multi-strands of drawn-filled tubes (DFT). Each strand is formed of a low resistance material and is encased in a high strength material (preferably, metal).

A selected number of "sub-strands" may be wound and coated with an insulative material. With regard to the operating environment of representative embodiments, such insulative material protects an individual conductor if its respective sheath is breached during use.

In addition to providing the requisite strength, flexibility, and resistance to fatigue, conductors 24 formed of multi-strands of drawn-filled tubes, in accordance with the above description, provide a low resistance alternative to other materials. Specifically, a stranded wire, or even a coiled wire, of approximately 60 cm and formed of MP35N or stainless steel or the like may have a measured resistance in excess of 30 ohms. In contrast, for the same length, a wire formed of multi-strands of drawn-filled tubes could have a resistance less than 4 ohms.

In the embodiment shown in FIG. 1C, the flexible paddle electrode array 11 includes five columns and four rows of electrodes 36, 38 arranged in a grid configuration, for a total of twenty electrodes 36, 38. As can be understood from FIG. 1C and as discussed in greater detail below, those columns may be three columns of non-flexible electrodes 36 and two columns of flexible electrodes 38, wherein the columns of non-flexible electrodes 36 are staggered more distally relative to the flexible electrodes 38.

Alternative numbers of columns and rows may be employed. For example, in some embodiments, thirty-two or more electrodes are distributed into multiple rows and multiple columns. Also, every row need not contain the same number of columns. For example, a number of rows can include a "tri-pole" design having three columns of electrodes while additional rows can include five or more columns of electrodes to enable a greater amount of electrical field resolution. Regardless of the number of columns and rows employed for the flexible paddle electrode array 11, as long as the non-flexible electrodes 36 and flexible electrodes 38 are arranged such that the flexible paddle electrode array 11 has transverse lines of reduced rigidity or stiffness at flex or hinge lines 100 discussed in detail below, the flexible paddle electrode array 11 will be able to flex or deflect along its length at those hinge lines 100, while maintaining the electrodes 36, 38 in adequate contact with the patient tissue.

The multiple columns of electrodes 36, 38 enable lateral control of the applied electrical field to stimulate the exact lateral position of the pertinent nerve fiber(s), as described herein. Specifically, it may be desirable to selectively stimulate a given dorsal column fiber that is associated with an afflicted region of the patient's body without affecting other regions of the patient's body. The multiple columns of electrodes according to representative embodiments provide sufficient resolution to relatively finely control the stimulation of one or several specific fibers, as described herein. Additionally, the multiple columns provide a degree of positional tolerance during the surgical placement of the flexible paddle electrode array 11 within the epidural space, as any one of the columns may be used to stimulate the pertinent nerve fiber(s). Also, if the flexible paddle electrode array 11 is displaced relative to the pertinent nerve fibers subsequent to implantation (e.g., due to lead migration), the stimulation pattern applied by a pulse generator can be shifted between columns to compensate for the displacement.

The multiple rows of electrodes 36, 38 enable multiple pain locations to be treated with a single implanted lead. Specifically, a first row can be used to treat a first pain complaint (e.g., pain in the lower extremities) and a second row can be used to treat a second pain location (e.g., post-laminectomy pain in the back). Furthermore, by separating the first and second rows by one or more "buffer" rows of high-impedance electrodes, the stimulation in the first and second rows may occur on a substantially independent basis. Specifically, anodes in the second row will have relatively minimal effect on the field distribution generated by cathodes in the first row.

In some embodiments, the flexible paddle electrode array 11 can be implanted within a patient such that electrodes 36, 38 are positioned within the cervical or thoracic spinal levels. After implantation, an electrode combination on a first row of electrodes can be determined that is effective for a first pain location with minimal effects on other regions of the body. The first pain location can be addressed by stimulating a specific dorsal column fiber due to the relatively fine electrical field resolution achievable by the multiple columns. Then, another electrode combination on a second row of electrodes can be determined for a second pain location with minimal effects on other regions of the body. The second pain location could be addressed by stimulating another dorsal column fiber as an example. After the determination of the appropriate electrodes for stimulation, a patient's IPG 310, which is depicted in FIG. 1C, can be programmed to deliver pulses using the first and second rows according to the determined electrode combinations.

When determining the appropriate electrode configurations, the selection of electrodes to function as anodes can often facilitate isolation of the applied electrical field to desired fibers and other neural structures. Specifically, the selection of an electrode to function as an anode at a position adjacent to another electrode functioning as a cathode causes the resulting electron/ion flow to be limited to tissues immediately surrounding the two electrodes. By alternating through a plurality of anode/cathode combinations it is possible to improve resolution in the stimulation of dorsal column fibers. Also, it is possible to confine the applied electrical field to or away from a periphery of the flexible paddle electrode array 11.

The operation of anodes can also be used to hyperpolarize neural tissue. Depending on the anode amplitude and the proximity to the pertinent neural tissue, the hyperpolarization can be used to prevent selected neural tissue from propagating action potentials. The hyperpolarization can also be used to prevent an adjacent cathode from initiating propagation of an action potential beginning at the selected neural tissue.

Multiple columns of electrodes 36, 38 also enable lateral "steering" of the electrical field using a single channel pulse generator. A single channel pulse generator refers to a pulse generator that provides an equal magnitude pulse to each active electrode at a given time. Specifically, each electrode is either "active" (i.e., it is coupled to the pulse generator output during pulse generation by a suitable gate or switch) or "inactive" (i.e., the gate or switch does not couple the electrode to the pulse generator output). Each "active" electrode experiences the same amplitude; only the polarity varies depending upon whether electrode is set as a cathode or anode as defined by positions of respective gates and/or switches. The steering of the electrical field occurs by selecting appropriate states for each of electrodes 36, 38.

The conductors 24 are carried in sheaths 15. In some embodiments, each sheath 15 carries eight conductors 24. With only two sheaths with eight conductors each, there would only be sixteen conductors. To accommodate the lower number of conductors than electrodes 36, 38, multiple electrodes may be coupled to the same conductor (and, hence, to a common terminal 22).

In some embodiments, other electrode designs can be employed to minimize the number of conductors 24 required to support the various electrodes 36, 38. For example, a relatively large number of electrodes (e.g., thirty-two, sixty-four, and greater) could be utilized on the flexible paddle electrode array 11. The electrodes could be coupled to one or several electrical gates (e.g., as deposited on a flex circuit). The electrical gates can be controllably configured to couple each electrode to a conductor carrying cathode pulses, to couple each electrode to an anode termination, or to maintain each electrode at a high impedance state. The electrical gates could be controlled using a main controller, such as a logic circuit, on the flexible paddle electrode array 11 that is coupled to a data line conductor 24. The data line conductor communicates signals from the IPG 310 that identify the desired electrode states, and the main controller responds to the signals by setting the states of the electrical gates as appropriate.

In another embodiment, a cathode conductor line 24 and an anode conductor line 24 are provided in one or several lead bodies 12 along with a plurality of optical fibers. The optical fibers are used to carry optical control signals that control the electrode states. Specifically, the flexible paddle electrode array 11 includes photodetectors (e.g., photodiodes) that gate connections to the anode conductor line and the cathode conductor line. The use of optical fibers to carry optical control signals may be advantageous, because the diameter of optical fibers suitable for such functionality is smaller than electrical conductors 24. Therefore, a larger number of electrodes (as compared to using a separate electrical conductor 24 for each electrode) can be independently controlled while maintaining the lead body diameters at an acceptable size.

The sheaths 15 and the paddle support structure 17 of the flexible paddle electrode array 11 are preferably formed from a medical grade, substantially inert material, for example, polyurethane, silicone, or the like. Importantly, such material should be non-reactive to the environment of the human body, provide a flexible and durable (i.e., fatigue resistant) exterior structure for the components of the paddle lead 10, and insulate adjacent terminals 22 and/or electrodes 36, 38.

The flexible paddle electrode array 11 may be fabricated to possess a substantially flat profile. Alternatively, the flexible paddle electrode array 11 may have an arcuate or bowed profile. In some embodiments, a wing structure or other type of stabilization structure extends along one or both longitudinal sides of the paddle structure 17. Such stabilization structures may be formed for the purpose of retaining the flexible paddle electrode array 11 within the central portion of the epidural space. In some embodiments, one or more electrodes 36, 38 may be disposed on the stabilization structures. Regardless of whether the flexible paddle electrode array 11 has a substantially flat profile or an arcuate profile or is equipped with one or more stabilization structures, as long as the non-flexible electrodes 36 and flexible electrodes 38 are arranged such that the flexible paddle electrode array 11 has transverse lines of reduced rigidity or stiffness at flex or hinge lines 100 discussed in detail below, the flexible paddle electrode array 11 will be able to flex or deflect along its length at those hinge lines 100, while maintaining the electrodes 36, 38 in adequate contact with the patient tissue.

As can be understood from FIGS. 1B and 1C, the paddle lead 10 is coupled to the IPG 310 by the lead connector assembly 18 of the paddle lead 10 being received in the header ports 311 of the IPG 310. Each header port 311 electrically couples the respective terminals 22 to a switch matrix (not shown) within the IPG 310.

The switch matrix selectively connects the pulse generating circuitry (not shown) of the IPG 310 to the terminals 22 of the paddle lead 10, and, hence to electrodes 36, 38. A sealed portion 312 of the IPG 310 contains pulse generating circuitry, communication circuitry, control circuitry, and a battery (not shown) within an enclosure to protect the components after implantation within a patient. The control circuitry may include a microprocessor, one or more application specific integrated circuits (ASICs), and/or any suitable circuitry for controlling the pulse generating circuitry. The control circuitry controls the pulse generating circuitry to apply electrical pulses to the patient via the electrodes 36, 38 of the flexible paddle electrode array 11 according to multiple pulse parameters (e.g., pulse amplitude, pulse width, pulse frequency, etc.). The electrodes 36, 38 are set to function as cathodes or anodes or set to a high-impedance state for a given pulse according to the couplings provided by the switch matrix. The electrode states may be changed between pulses.

When the paddle lead 10 is initially implanted within the patient, a determination of the set(s) of pulse parameters and the electrode configuration(s) that may effectively treat the patient's condition is made. The determination or programming typically occurs through a physician's interaction with configuration software 321 executed on the programmer device 320, as indicated in FIG. 1B. The configuration software 321 steps the physician through a number of parameters and electrode configurations based on a trolling algorithm. In some embodiments, the electrode configurations are stepped through by laterally "steering" the electrical field by moving the anodes and/or cathodes along a row of the paddle. The patient provides feedback to the physician regarding the perceived stimulation that occurs in response the pulse parameters and electrode configuration(s). The physician may effect changes to the parameters and electrode configuration(s) until optimal pulse parameters and electrode configuration(s) are determined. The final pulse parameters and configurations are stored within the IPG 310 for subsequent use. The pulse parameters and configurations are used by the IPG 310 to control the electrical stimulation provided to the patient via the paddle lead 10. Although single channel IPGs have been described according to some embodiments, multiple current or voltage source IPGs could alternatively be employed.

D. FLEXIBLE PADDLE ELECTRODE ARRAY

Figure 2:
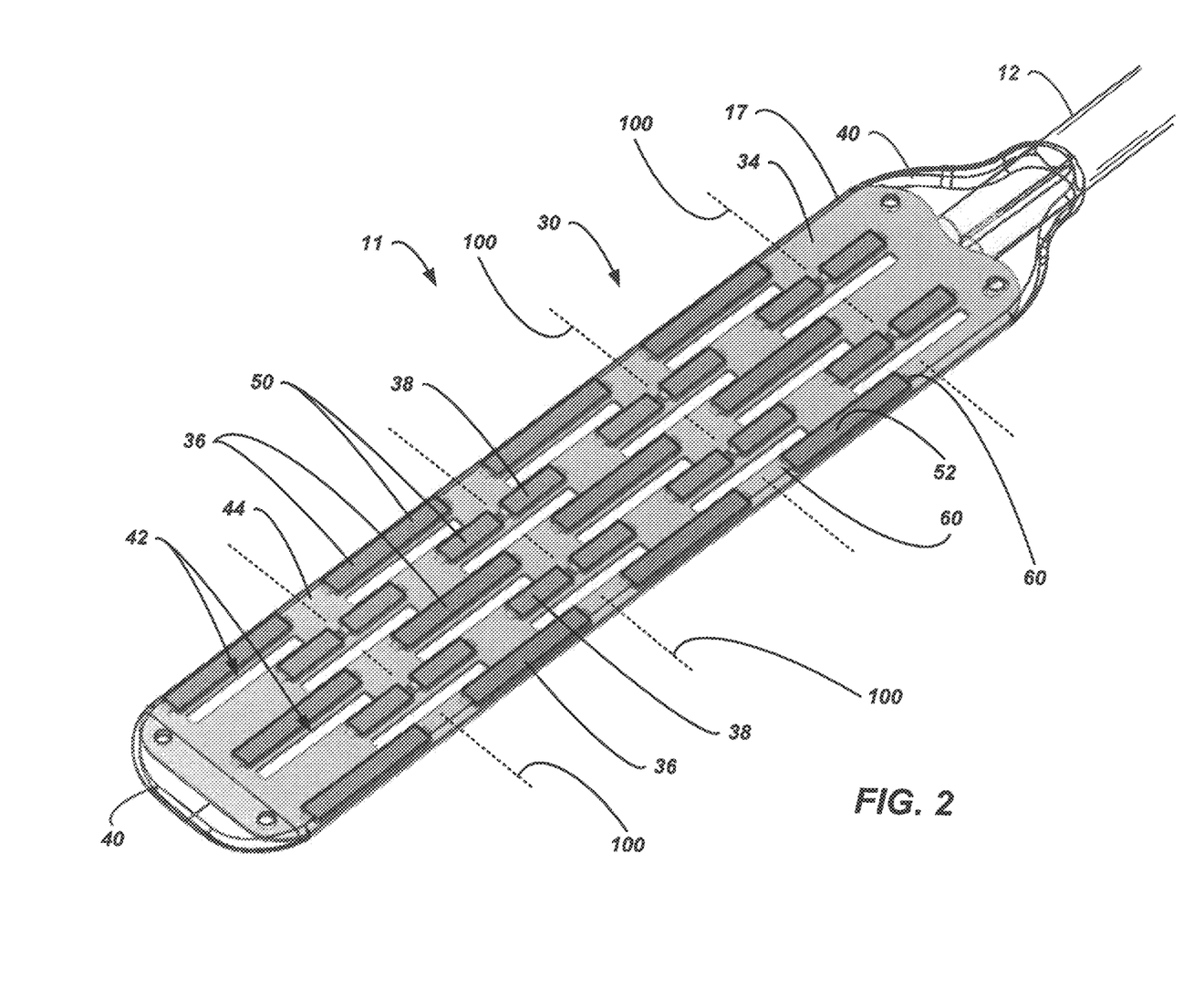
FIG. 2 is an isometric view of the flexile paddle electrode array of the paddle lead of FIG. 1C, as viewed from a patient contact side of the flexile paddle electrode array.
Figure 3:
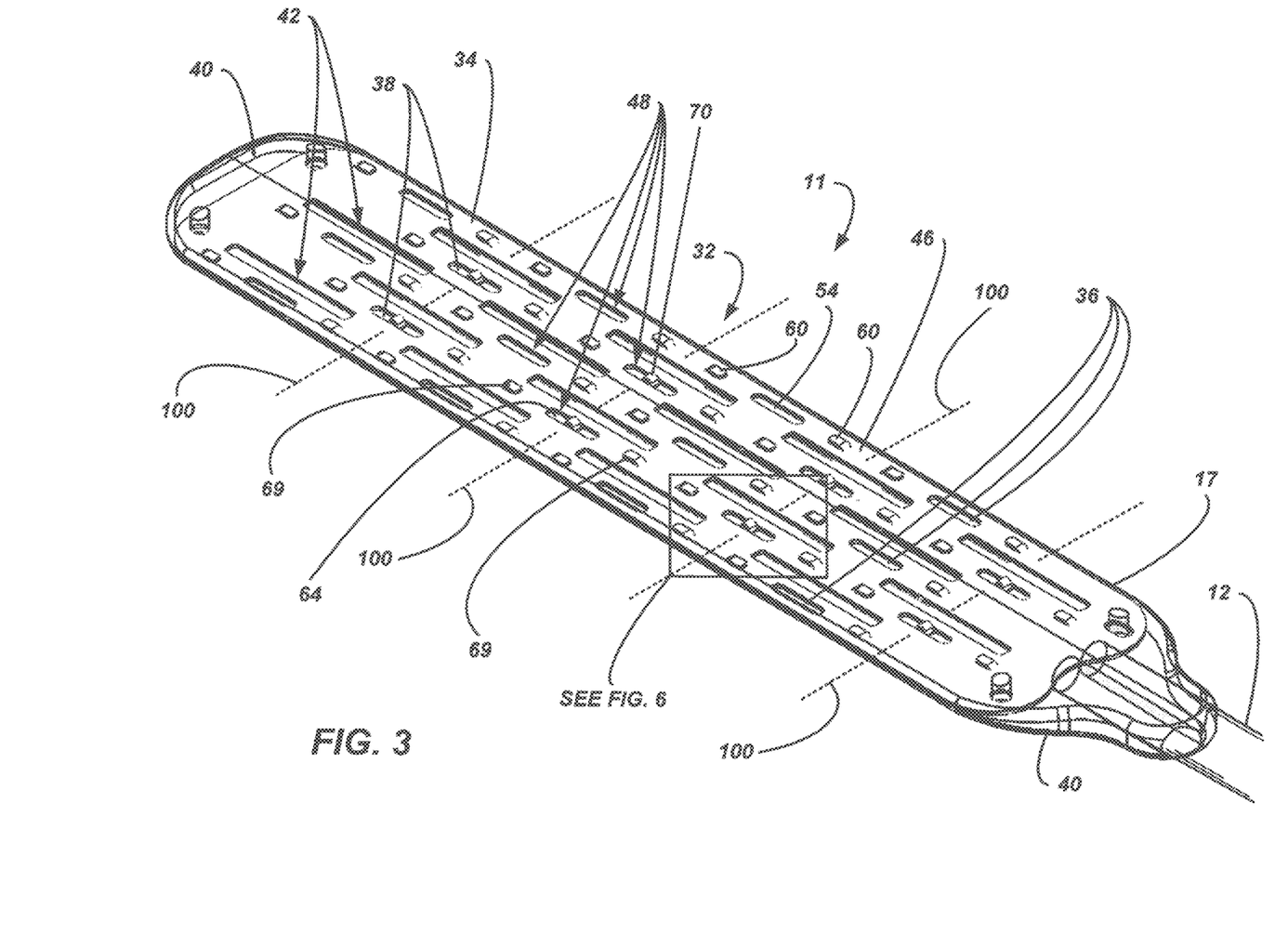
FIG. 3 is an isometric view of the flexile paddle electrode array of FIG. 2, except as viewed from an electrically insulated side of the flexile paddle electrode array opposite the patient contact side illustrated in FIG. 2.

FIG. 2 is an isometric view of the flexile paddle electrode array 11 of the lead of FIG. 1C, as viewed from a patient contact side 30 of the array 11. FIG. 3 is an isometric view of the array 11 of FIG. 2, except as viewed from an electrically insulated side 32 of the array 11 opposite the patient contact side 30 illustrated in FIG. 2. As shown in FIGS. 2 and 3, the paddle electrode array 11 includes a planar flexible substrate 34, non-flexible electrodes 36, flexible electrodes 38, and an enclosure 40. The planar flexible substrate 34 and enclosure 40 can be said to form a substantially flat and thin paddle style structure 17. The nonflexible electrodes 36 and flexible electrodes 38 are arranged within the paddle style structure 17. The electrodes 36, 38 are mutually separated by the electrically insulative material of the paddle 17.

The planar flexible substrate 34 may be formed of polyether ether ketone (PEEK), Fiberglass, or Liquid Crystal Polymer. The substrate 34 may have a thickness of between approximately 0.007" and approximately 0.1", a width of between approximately 0.37" and approximately 0.5", and a length of between approximately 0.7" and approximately 2.0". The substrate 34 includes a patient contact side 44 and an electrically insulated side 46 opposite the patient contact side 44. These sides 44, 46 of the substrate 34 respectively correspond to the patient contact side 30 and the electrically insulated side 32 of the array 11.

As illustrated in FIGS. 2 and 3, longitudinally extending long slots 42 extend through the thickness of the substrate 34 to daylight at the patient contact side 44 and opposite electrically insulated side 46 of the substrate 34. The long slots 42 run parallel to a longitudinal axis of the flexible paddle electrode array 11. The long slots 42 have a length of between approximately 0.20" and approximately 0.30" and a width of between approximately 0.025" and approximately 0.38".

Similarly, as can be understood from FIG. 3, longitudinally extending short slots 48 extend through the thickness of the substrate 34 to daylight at the patient contact side 44 and opposite electrically insulated side 46 of the substrate 34, although, as can be understood from FIGS. 2 and 3, the short slots 48 are hidden by the electrodes 36, 38 on the patient contact side 44 of the substrate 40. The short slots 48 run parallel to the longitudinal axis of the flexible paddle electrode array 11. The short slots 48 have a length of between approximately 0.05" and approximately 0.10" and a width of between approximately 0.015" and approximately 0.025".

Except as noted below, the enclosure 40 extends coextensively about the entirety of all surfaces of the substrate 34 and the electrodes 36, 38 supported on the substrate 34. The exception to this statement is the planar faces 50 of the electrodes 36, 38 on the patient contact side 30 of the paddle 11. These electrode faces 50 extend through the enclosure 40 to be exposed for making electrical contact with patient tissue, as can be understood from FIG. 2.

As can be understood from FIGS. 1C-3, the paddle electrode array 11 extends from the lead body 11. The enclosure 40 may be a continuous or generally continuous extension of one or more insulation layers of the jacket of the lead body 12. The jacket of the lead body 12 and the enclosure 40 may be in the form of one or more insulation layers. Such insulation layers may be fabricated of silicone rubber, polyurethane, silicone rubber-polyurethane-copolymer (SPC), polytetrafluoroethylene ("PTFE"), and/or other suitable polymers. The lead body 12 and electrode array 11 include many internal components, including electrical conductors 24 extending through the lead body 12 and electrode array 11 from the electrical contacts 22 of the lead connector assembly 18 to the electrodes 36, 38 supported on the electrode array 11. The insulation layers of the lead body 12 and enclosure 40 isolate these internal components of the lead body 12 and paddle array 11 from each other and the surrounding environment.

The patient contact side 30 includes exposed electrode faces 50 that are configured to contact patient tissue and administer electrical energy to the patient tissue and/or sense electrical signals from the patient tissue. The electrically insulated side 32 of the array 11 is opposite from the patient contact side 30 and has a continuous and unbroken layer of the enclosure 40 extending over it such that no electrical contact can be established with the electrodes 36, 38 by patient tissue coming into contact with the electrically insulated side 32.

Figures 4A, 4B:
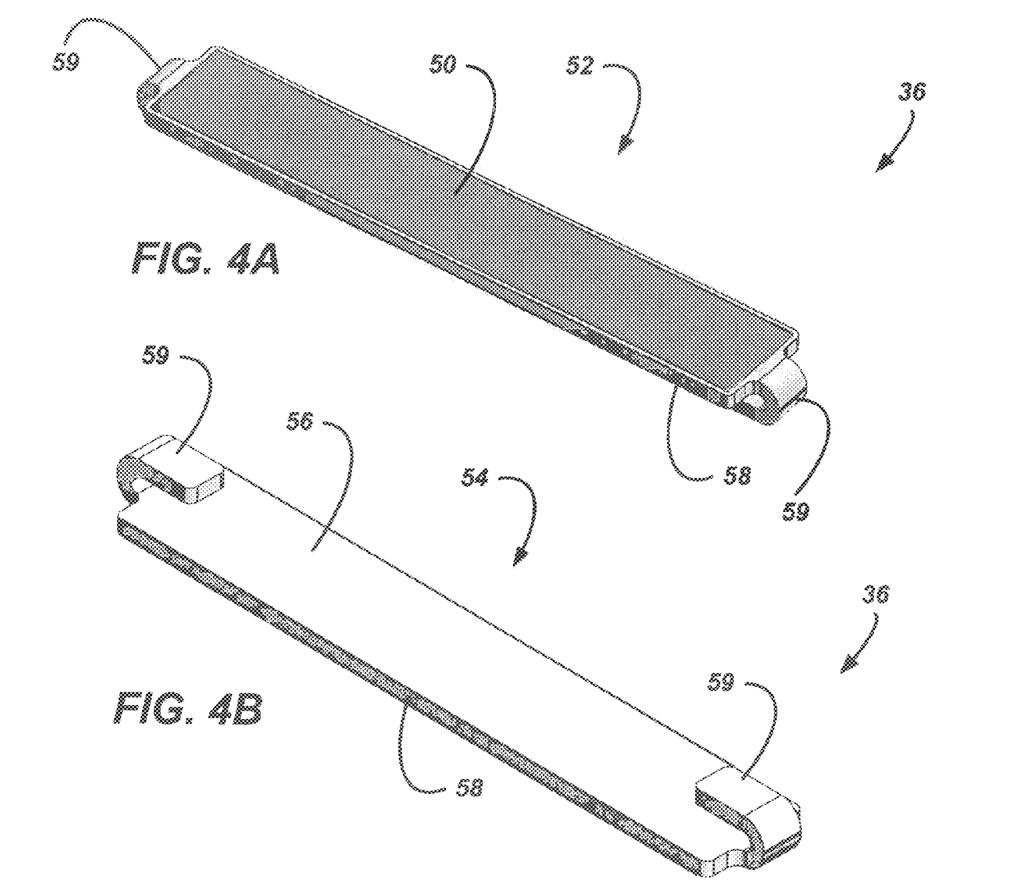
FIG. 4A is an isometric view of an outer or patient contact side of a nonflexible electrode of the flexible paddle electrode array of FIG. 2.
FIG. 4B is an isometric view of an inner side of the nonflexible electrode of FIG. 4A, the inner side being opposite the patient contact side.
Figure 4C:
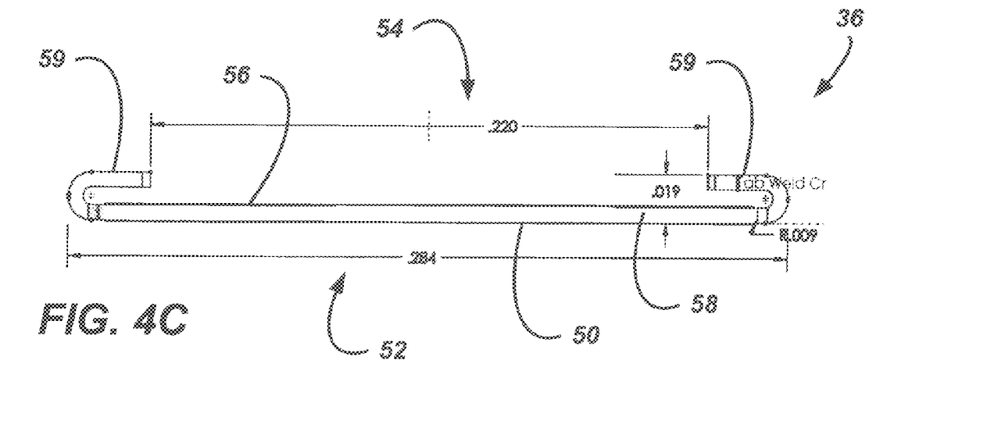
FIG. 4C is a side elevation view of the nonflexible electrode of FIG. 4A.

For a discussion regarding the nonflexible electrodes 36 employed in the electrode array 11, reference is made to FIGS. 4A-4C. FIG. 4A is an isometric view of an outer or patient contact side 52 of a nonflexible electrode 36 of the flexible paddle electrode array 11 of FIG. 2. FIG. 4B is an isometric view of an inner side 54 of the nonflexible electrode 36 of FIG. 4A, the inner side 54 being opposite the patient contact side 52. FIG. 4C is a side elevation view of the nonflexible electrode 36 of FIG. 4A.

As shown in FIGS. 4A-4C, the patient contact side 52 of the nonflexible electrode 36 includes a planar face 50, and the inner side 54 of the nonflexible electrode 36 includes another planar face 56 opposite the planar face 50 of the patient contact side 52. As illustrated in FIG. 2, the planar face 50 of the patient contact side 52 is not covered by the enclosure 40 and, as a result, serves as the exposed surface 50 of the electrode 36 through which the electrode 36 administers and/or senses electrical signals. As can be understood from FIGS. 2, 3 and 6, which is an enlarged area of FIG. 3, the planar face 56 of the inner side 54 abuts against the patient contact side 44 of the substrate 34 in generally planar surface contact. While a short slot 48 may open underneath the planar face 56 of the inner side 54, the enclosure 40 extends over the entirety of the electrically insulated side 46 of the substrate 34. As a result, the planar face 56 of the inner side 54 is electrically isolated and does not serve as a surface through which the electrode 36 may administer and/or sense electrical signals.

As indicated in FIGS. 4A-4C, the nonflexible electrode 36 includes a single continuous rectangular body 58 that includes the two planar surfaces 50, 56. At the opposite ends of the body 58 are folded over tabs 59. As can be understood from FIGS. 2 and 3, these tabs 59 may be employed for welding or otherwise affixing the electrode 36 to the substrate 34 and the respective electrical conductors 24 that extend from the contacts 22 of the lead connector assembly 18 and through the body 12 and array 11 to the electrode 36.

Figures 5A, 5B:
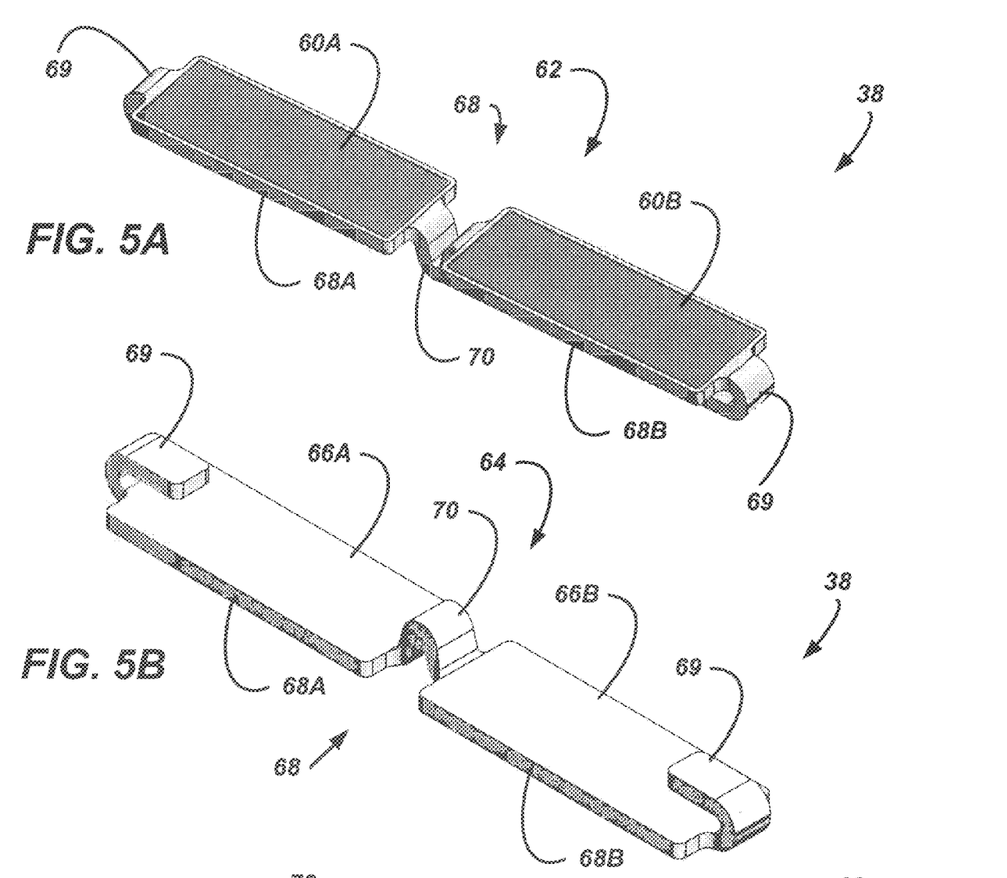
FIG. 5A is an isometric view of an outer or patient contact side of a flexible electrode of the flexible paddle electrode array of FIG. 2.
FIG. 5B is an isometric view of an inner side of the flexible electrode of FIG. 5A, the inner side being opposite the patient contact side 62.
Figure 5C:
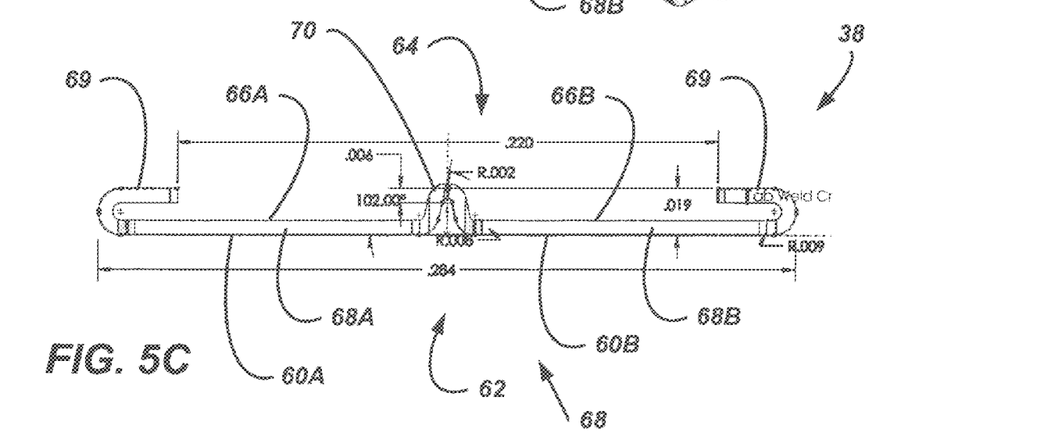
FIG. 5C is a side elevation view of the flexible electrode of FIG. 5A.

For a discussion regarding the flexible electrodes 38 employed in the electrode array 11, reference is made to FIGS. 5A-5C. FIG. 5A is an isometric view of an outer or patient contact side 62 of a flexible electrode 38 of the flexible paddle electrode array 11 of FIG. 2. FIG. 5B is an isometric view of an inner side 64 of the flexible electrode 38 of FIG. 5A, the inner side 64 being opposite the patient contact side 62. FIG. 5C is a side elevation view of the flexible electrode 38 of FIG. 5A.

As indicated in FIGS. 5A-5C, the flexible electrode 38 includes a discontinuous or segmented rectangular body 68 having a first rectangular body segment 68A joined via a flexible bridge 70 to a second rectangular body segment 68B. Each body segment 68A, 68B includes a respective pair of planar surfaces 60A, 68A and 69B, 68B.

As illustrated in FIG. 5C, the flexible bridge 70 is V-shaped or U-shaped and protrudes outwardly from the inner side 64 of the electrode 38. As shown in FIGS. 5A-5C, the U-shaped flexible bridge 70 is approximately the same thickness as the body segments 68A, 68B, but has a width that is approximately half as wide or less than the width of the body segments 68A, 68B. The U-shaped flexible bridge 70 has arcuate or curved transitions between itself and the adjoining body segments 68A, 68B. Further the U-shaped flexible bridge 70 has an arcuate or curved transition at its extreme apex, which projects outwardly from the inner side 64 of the electrode 38 a distance that slightly exceeds that of the tabs 69.

Folded over tabs 69 are at the opposite ends of the segmented body 68. As can be understood from FIGS. 2, 3 and 6, these tabs 69 may be employed for welding or otherwise affixing the electrode 38 to the substrate 34 and the respective electrical conductors 24 that extend from the contacts 22 of the lead connector assembly 18 and through the body 12 and array 11 to the electrode 38.

As shown in FIGS. 5A-5C, the patient contact side 62 of the flexible electrode 38 includes planar faces 60A, 60B. Each such face 60A, 60B is part of a respective rectangular body segment 68A, 68B. Similarly, the inner side 64 of the flexible electrode 38 includes planar faces 66A, 66B opposite the planar faces 60A, 60B of the patient contact side 62. Each such face 66A, 66B is part of a respective rectangular body segment 68A, 68B.

As illustrated in FIG. 2, the planar faces 60A, 60B of the patient contact side 62 are not covered by the enclosure 40 and, as a result, serve as the exposed surfaces 60A, 60B of the flexible electrode 38 through which the flexible electrode 38 administers and/or senses electrical signals. As can be understood from FIGS. 2, 3 and 6, the planar faces 66A, 66B of the inner side 64 abut against the patient contact side 44 of the substrate 34 in generally planar surface contact. While a short slot 48 opens underneath the planar faces 66A, 66B of the inner side 64, and while the flexible bridge 70 extends through the short slot 48, the enclosure 40 extends over the entirety of the electrically insulated side 46 of the substrate 34. As a result, the planar faces 66A, 66B of the inner side 64 and the flexible bridge 70 are electrically isolated and do not serve as surfaces through which the electrode 38 may administer and/or sense electrical signals.

As can be understood from FIGS. 2, 4A-4C, and 5A-5C, in one embodiment, each nonflexible electrode 36 has an overall length of between approximately 0.18" and approximately 0.28", and an overall width of between approximately 0.026" and approximately 0.042". Each flexible electrode 38 has an overall length of between approximately 0.26" and approximately 0.29", and an overall width of between approximately 0.026" and approximately 0.042".

Each electrode segment 68A, 68B has an overall length of between approximately 0.11" and approximately 0.12".

Each flexible electrode 38 also has a gap distance over which the bridge 70 extends between immediately adjacent ends of the segments 68A, 68B that is between approximately 0.02" and approximately 0.03".

End-to-end spacing between immediately adjacent electrodes in the same column is between approximately 0.08" and approximately 0.2". Side-to-side spacing between immediately adjacent electrode columns is between approximately 0.02" and approximately 0.04".

The electrodes 36, 38 are formed of an electrically conductive and biocompatible material. Examples of such candidate electrode materials include stainless steel, MP35N, platinum, and platinum alloys. In one embodiment, the electrodes 36, 38 are formed of a platinum-iridium alloy.

As can be understood from FIGS. 1C-6, the implantable therapy lead 10 includes a flexible paddle electrode array 11 with flexible electrodes 38. Each flexible electrode 38 has a segmented configuration having first and second electrode segments 68A, 68B and a flexible bridge or living hinge 70 joining together the first and second electrode segments 68A, 68B. As noted above, the flexible bridge 70 may be V-shaped or U-shaped and have a width that is less than a width of the first electrode segment 68A or the second electrode segment 68B.

In one embodiment, the flexible electrode 38 is of an integrated construction such that the electrode segments 68A, 68B and the living hinge 70 are manufactured of one or more individual pieces that are joined together via, for example, welding or crimping. In another embodiment, the flexible electrode 38 is of a unitary and continuous construction such that the electrode segments 68A, 68B and the living hinge 70 are formed from a single piece of material via stamping, laser cutting or other methods. As a result, the flexible electrode 38 have a unitary construction such that the segments 68A, 68B and the living hinge 70 are not individual components that are joined together during the manufacturing process, but are of a single, unitary and continuous piece of material to form a flexible electrode 38 of a continuous and unitary construction.

Regardless of how the flexible electrode 38 is manufactured and regardless of whether it is of an integrate construction or an integral construction, the living hinge 70 allows the flexible electrode 38 to flex along the hinge 70 while still being a one-piece electrode 38. Accordingly, the flexible electrode 38 only requires a single feeder electrical conductor contact and does not require a jumper wire between the two electrode segments 68A, 68B.

Figure 6:
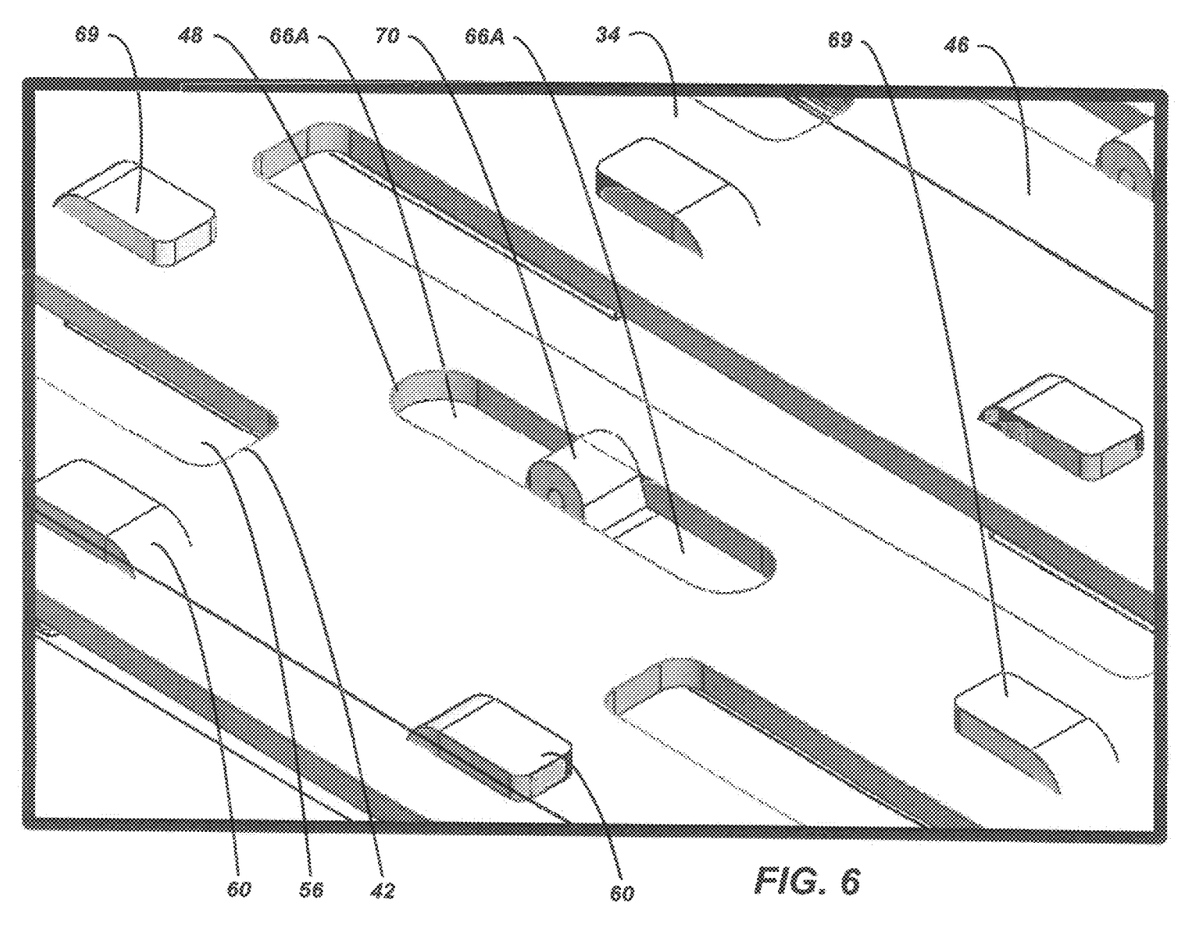
FIG. 6 is an enlarged view of a region of FIG. 3.

The flexible paddle electrode array 11 also includes a substrate 34 on which the flexible electrodes 38 are supported. The substrate 34 includes a short slot 48 that extends through the thickness of the substrate 34, and the flexible bridge 70 is located in the short slot 70, as shown in FIG. 6.

As illustrated in FIGS. 2-3, the flexible paddle electrode array 11 also includes nonflexible electrodes 36 that do not extend across flex lines 100 of the flexible paddle electrode array 11. The flex lines 100 extend generally perpendicular to the longitudinal length of the array 11 to pass through the flexible bridges 70. In other words, the flex lines 100 extend laterally across the array 11 to pass through the flexible bridges 70.

The flex lines 100 may be considered lines of reduced stiffness or rigidity in the flexible paddle electrode array 11 on account of the reduced stiffness or rigidity provided by the laterally aligned living hinges 70. The flex lines 100 are locations along the length of the flexible paddle electrode array 11 where the flexible paddle electrode array 11 can flex. Because the nonflexible electrodes 36 do not extend across the flex lines 100, and the flexible bridges 70 of the flexible electrodes 38 are aligned with the flex lines 100 such that the bridges 70 can act as living hinges 70 to allow the electrode segments 68A, 68B (see FIGS. 5A-5C) of the flexible electrodes 38 to flex relative to each other at their respective living hinges 70, the flexible paddle electrode array 11 can flex or bend along the various flex lines 100. Thus, as can be understood from FIGS. 2 and 3, the flexible electrodes 38 allow for staggered rows of electrodes on the flexible paddle electrode array without increasing stiffness between the rows of electrodes.

As indicated in FIGS. 2 and 3, the flexible electrodes 38 are part of a plurality of flexible electrodes 38 evenly spaced along at least one column line (i.e., longitudinally extending line) that is generally parallel with a longitudinal axis of the flexible paddle electrode array 11. Similarly, the nonflexible electrodes 36 are part of a plurality of nonflexible electrodes 36 evenly spaced along at least another column line (i.e., longitudinally extending line) that is generally parallel with the longitudinal axis of the flexible paddle electrode array 11.

These column lines of flexible electrodes 38 and nonflexible electrodes 36 are laterally offset from each other. In one embodiment, there may be two column lines of flexible electrodes 38 and three column lines of nonflexible electrodes 36. The column lines of flexible electrodes 38 and nonflexible electrodes 36 are arranged in an alternating configuration running laterally across the flexible paddle electrode array 11. The flexible electrodes 38 are evenly spaced apart from each other, as is also the case with the nonflexible electrodes 36. The flexible electrodes 38 are staggered along a length of the flexible paddle electrode array 11 relative to the nonflexible electrodes 36. In one embodiment, each of the two column lines of flexible electrodes 38 includes four flexible electrodes 38, and each of the three column lines of nonflexible electrodes 36 includes four nonflexible electrodes 36. Such an embodiment can also be said to have four row lines (i.e., transversely extending lines) of two flexible electrodes 38 that are laterally or transversely space apart from each other, and four row lines (i.e., transversely extending lines) of three nonflexible electrodes 36 that are laterally or transversely spaced apart from each other, as can be understood from FIG. 2.

Figure 7A:
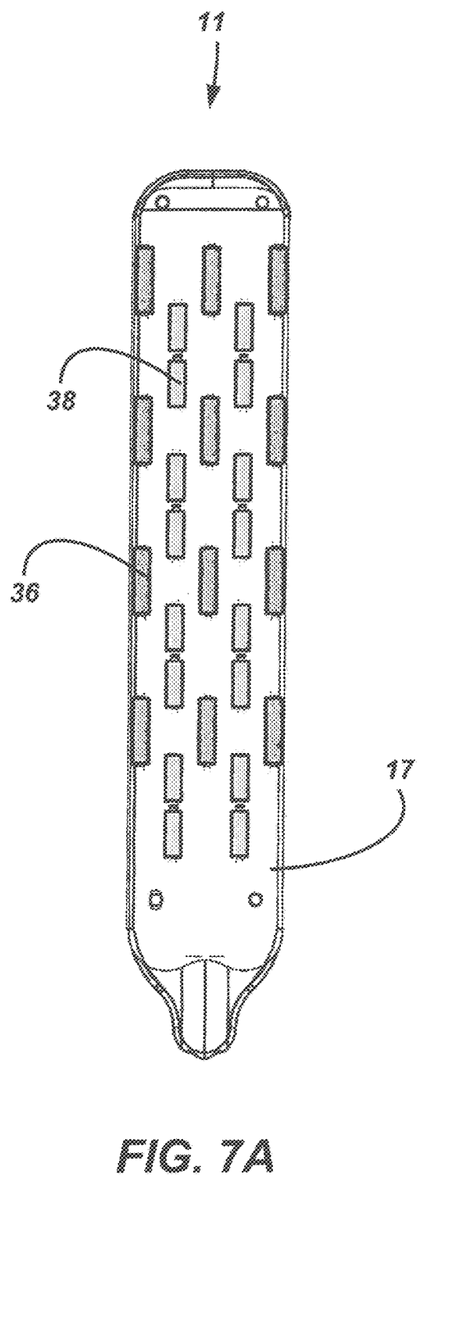
FIGS. 7A and 7B are plan views of a shortened coverage electrode array and an elongated electrode array, respectively.

The flexible paddle electrode array 11 and its components can be configured as depicted in FIGS. 1C-6 and dimensioned as discussed above. In other embodiments, the array 11 and its components may have other arrangements. For example, as illustrated in FIG. 7A, in one embodiment, the flexible paddle electrode array 11 may employ an electrode array that is shortened or longitudinally compressed. The paddle structure 17 can be curved or flat. The electrode array may extend over a longitudinal length of approximately 37 mm and, as a result, be substantially short of the full length of the underlying paddle structure 17. The paddle structure 17 may have a width of approximately 9.5 mm and the array width may be approximately 9 mm. Electrode column spacing and electrode row spacing may be approximately 1 mm and approximately 5 mm, respectively. The electrodes 36, 38 may be approximately 4 mm long by approximately 1 mm wide. The nonflexible electrodes 36 may be longitudinally staggered relative to the flexible electrodes 38 with stagger overlap of approximately 0.5 mm.

Figure 7B:
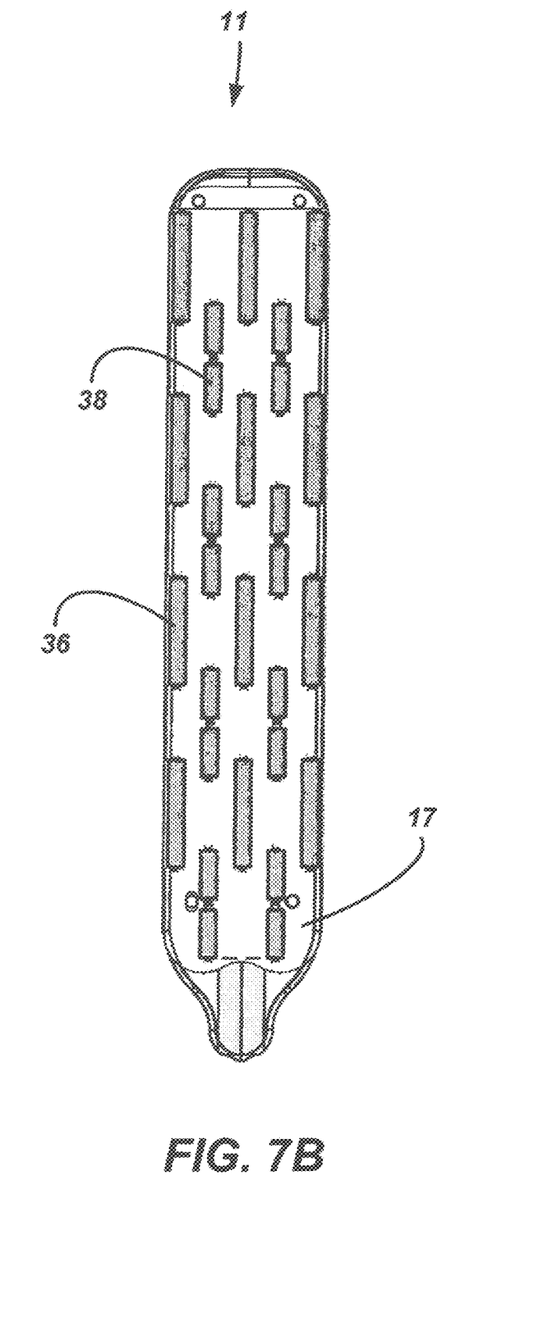

In another embodiment, as depicted in FIG. 7B, the flexible paddle electrode array 11 may employ an electrode array that is elongated or longitudinally extended. The paddle structure 17 can be curved or flat. The electrode array may extend over a longitudinal length of approximately 45 mm and, as a result, extend nearly the full length of the underlying paddle structure 17. The paddle structure 17 may have a width of approximately 9.5 mm and the array width may be approximately 9 mm. Electrode column spacing and electrode row spacing may be approximately 1 mm and approximately 4.5 mm, respectively. The electrodes 36, 38 may be approximately 6.5 mm long by approximately 1 mm wide. The nonflexible electrodes 36 may be longitudinally staggered relative to the flexible electrodes 38 with stagger overlap of approximately 1 mm.

In general, while the invention has been described with reference to particular embodiments, modifications can be made thereto without departing from the spirit and scope of the invention.

What is claimed is:

1. A neurostimulation system comprising:
an implantable pulse generator; and
an implantable therapy lead configured to be electrically coupled to the implantable pulse generator and comprising a flexible paddle electrode array comprising:
a row of laterally aligned flexible electrodes, the row of laterally aligned flexible electrodes at least partially contributing to the formation of a flex line in the flexible paddle electrode; and
a row of laterally aligned nonflexible electrodes longitudinally offset from the row of laterally aligned flexible electrodes such the flex line does not extend across the row of laterally aligned nonflexible electrodes.

2. The system of claim 1, wherein a flexible electrode of the flexible electrodes comprises a first electrode segment and a second electrode segment spaced-apart from the first electrode segment, the flex line passing between the spaced-apart first and second electrode segments.

3. The system of claim 2, wherein the flexible electrode of the flexible electrodes further comprises a flexible living hinge joining the spaced-apart first and second electrode segments, the flex line passing through the flexible living hinge and further wherein the flexible electrode is of unitary and continuous construction such that the first electrode segment, the second electrode segment and the flexible living hinge are formed from a single material piece during manufacturing of the flexible electrode; and
wherein the forming during manufacturing of the flexible electrode comprises at least one of stamping or laser cutting.

4. The system of claim 3, wherein the flexible living hinge comprises a V-shape or U-shape.

5. The system of claim 3, wherein the flexible electrode is of an integrated construction such that at least one of the first electrode segment, the second electrode segment or the flexible living hinge are separate pieces joined together during manufacturing of the flexible electrode and further wherein the joining together during manufacturing of the flexible electrode comprises at least one of welding or crimping.

* * * * *